United States Patent [19]

Marx

[11] Patent Number: 4,547,366

[45] Date of Patent: Oct. 15, 1985

[54] AQUEOUS WOOD PRESERVATIVE

[75] Inventor: Hans-Norbert Marx, Buehl-Weitenung, Fed. Rep. of Germany

[73] Assignee: BASF Aktiengesellschaft, Fed. Rep. of Germany

[21] Appl. No.: 625,980

[22] Filed: Jun. 29, 1984

Related U.S. Application Data

[63] Continuation of Ser. No. 249,688, Mar. 31, 1981, abandoned.

[30] Foreign Application Priority Data

Apr. 14, 1980 [DE] Fed. Rep. of Germany ....... 3014194

[51] Int. Cl.$^4$ ............................................. A01N 43/50
[52] U.S. Cl. ...................................... 424/78; 514/395; 514/461; 514/471; 514/493; 514/552; 514/747
[58] Field of Search ........................................... 424/78

[56] References Cited

U.S. PATENT DOCUMENTS

| | | | |
|---|---|---|---|
| 2,204,009 | 6/1940 | Bruson | 424/78 |
| 3,214,279 | 10/1965 | Scott | 424/78 |
| 3,227,563 | 1/1966 | Fahlstrom | 424/78 |
| 3,308,082 | 3/1967 | Pauli et al. | 424/78 |
| 3,778,512 | 12/1973 | Krenzer et al. | 424/285 |
| 3,993,772 | 11/1976 | Pommer et al. | 424/285 |

*Primary Examiner*—Leonard Schenkman
*Attorney, Agent, or Firm*—Keil & Weinkauf

[57] ABSTRACT

A wood preservative which consists of an aqueous solution containing both an alkyd resin and a fungicidal or insecticidal active ingredient, namely 2,5-dimethylfuran-3-carboxylic acid N-methoxy-N-cyclohexylamide, tributyl-tin benzoate, tributyl-tin naphthenate, gamma-hexachlorocyclohexane, pentachlorophenol laurate, 2-methoxycarbonylamino-benzimidazole or a mixture of these active ingredients.

5 Claims, No Drawings

AQUEOUS WOOD PRESERVATIVE

This is a continuation of application Ser. No. 249,688, filed Mar. 31, 1981 now abandoned.

The present invention relates to an aqueous wood preservative consisting of an aqueous solution which contains both an alkyd resin and a fungicidal or insecticidal active ingredient.

The use of 2,5-dimethylfuran-3-carboxylic acid N-methoxy-N-cyclohexylamide as a fungicide is disclosed in German-Laid-Open Application DOS 2,455,082. Further, it is known in that in water-soluble alkyd resins, especially neutralized alkyd resins, may be used, in aqueous solution, as water-based wood finishes (Römpp, Chemie-Lexikon, 7th Edition, Volume 1, pages 120–121, and Volume 6, page 3884).

It is also known that tributyl-tin benzoate, tributyl-tin naphthenate, gamma-hexachlorocyclohexane, pentachlorophenol laurate, the potassium salt of N-cyclohexyl-N-hydroxy-diazenium oxide, the sodium salt of 2-mercaptobenzthiazole, the sodium salt of 8-hydroxyquinoline, and 2-methoxycarbonylamino-benzimidazole are useful as active ingredients in fungicides or insecticides.

We have found that an aqueous solution which contains both an alkyd resin and a fungicidal or insecticidal active ingredient, namely 2,5-dimethylfuran-3-carboxylic acid N-methoxy-N-cyclohexylamide, tributyl-tin benzoate, tributyl-tin naphthenate, gamma-hexachlorocyclohexane, pentachlorophenol laurate, 2-methoxycarbonylamino-benzimidazole or a mixture of these active ingredients, is useful as a wood preservative. It is surprising that even those of the above compounds which are water-insoluble will dissolve in water in the presence of an alkyd resin and retain their well-known good fungicidal and insecticidal activity in such solution. The novel wood preservatives contain, for example, from 0.5 to 5 percent by weight, especially from 1 to 4 percent by weight, of active ingredient and from 5 to 40 percent by weight, especially from 10 to 30 percent by weight, of alkyd resin, in aqueous solution, the percentages being based on the final mixture. Preferred alkyd resins are neutralized water-soluble alkyd resins. Neutralization may be effected with an alkali, e.g. sodium hydroxide or potassium hydroxide or ammonia, in aqueous solution. The preferred active ingredient is 2,5-dimethylfuran-3-carboxylic acid N-methoxy-N-cyclohexylamide.

To improve the effectiveness of the novel preservatives, the active ingredients present in them may also be mixtures of the above ingredients with other conventional ingredients, for example with the potassium salt of N-cyclohexyl-N-hydroxide-diazenium oxide, the sodium salt of 2-mercaptobenzthiazole, the sodium salt of 8-hydroxyquinoline, carbamates or phosphoric acid esters.

The novel wood preservatives may additionally contain surfactants, for example alkylene oxide adducts, e.g. adducts of ethylene oxide or propylene oxide with, in particular, alkylphenols; the amounts of such adducts may be from 0.1 to 5 percent by weight, especially from 0.5 to 3 percent by weight. An adduct of from 8 to 11 moles of ethylene oxide with 1 mole of nonylphenol is preferred.

The novel wood preservatives may in addition contain conventional driers (siccatives) (Römpp, Chemie-Lexikon, 7th Edition, Volume 6, pages 3692–3693), for example in amounts of from 0.5 to 3 percent by weight, especially from 1 to 2 percent by weight. A preferred drier is a mixture of the octoates of cobalt, manganese and lead.

The novel wood preservatives may also contain conventional finely divided pigments (Römpp, Chemie-Lexikon, 7th Edition, Volume 4, pages 2693–2695), e.g. organic or inorganic pigments, for example in amounts of from 1 to 10 percent by weight, especially from 2 to 5 percent by weight. Furthermore, they may contain organic liquids, e.g. hydrocarbons or glycols, for example in amounts of from 3 to 10 percent by weight, especially from 6 to 8 percent by weight. Preferred liquids are a gasoline fraction of boiling range 180°–220° C., and butylglycol.

The use of aqueous dispersions of plastics in the preparation of wood surface-coating agents is disclosed in German Published Application DAS 1,642,171. Such dispersions are in general distinguished by rapid drying and high resistance to weathering.

Further, it is known that water-dilutable synthetic resins, especially neutralizable and consequently water-soluble alkyd resins, may be used in wood surface-coating agents. Such materials are again distinguished by rapid drying and high weathering resistance. Both categories of agents have the advantage that they contain little or no organic solvent and accordingly conform especially well to the ecological need to minimize solvent pollution of the environment, and that they do not burn.

Hitherto, however, these agents have found little use in wood preservation in the true sense, since most of the active ingredients used in such preservation are insoluble in water and hence substantial amounts of auxiliary solvents would be necessary to cause them to dissolve in water. Such auxiliary solvents, however, would annul the above advantages of the aqueous coating agents.

In preparing the novel wood preservatives it is possible, for example, to mix a 10% strength by weight aqueous solution of the alkyd resin, neutralized with sodium hydroxide solution or potassium hydroxide solution, ammonia or an organic amine, directly with 100% strength 2,5-dimethylfuran-3-carboxylic acid N-methoxy-N-cyclohexylamide, or with a 50% strength solution thereof in a gasoline fraction, without using an additional solvent. Completely homogenous, clear to slightly cloudy mixtures are obtained. Even on prolonged storage, these mixtures do not change, i.e. the active ingredient does not separate out.

Surprisingly, certain other conventional biologically active substances which are inherently water-insoluble can, in this way, be dissolved in water.

Many other conventional active ingredients useful in wood preservation and belonging to the category of the insecticides, or to the category of the fungicides which are effective against wood-destructive or wood-discoloring fungi, may additionally be present in the novel wood preservatives.

In use, the novel wood preservative penetrates uniformly into the wood. This therefore avoids the disadvantages of two-phase system (dispersion systems) and dispenses with the use of additional organic solvents.

A further important aspect is that the novel wood preservatives are non-flammable and have a very low odor. Depending on the concentration of the alkyd resin in the wood preservative, the formulation constitutes an impregnating primer, open-pore preservative glaze or thick glaze, the stated sequence corresponding to increasing concentration of the resin.

It is also possible to disperse pigments or pigment formulations in the wood preservatives, so that when the wood is treated not only a preservative effect but also a decorative effect is achieved.

The alkyd resins are normally available as solutions in organic solvents and may be used as such, or in a solvent-free form. In the former case, the total solvent content of the finished wood preservative is 3–10%, the solvent generally being a glycol derivative.

For the experiments to be described, an alkyd resin was used; this resin is produced from phthalic acid or phthalic anhydride, glycerol and saturated fatty acids, e.g. palmitic acid or stearic acid.

The formulation examples which follow illustrate the composition of the novel wood preservatives.

(1) Colorless wood primer, affording preventive protection against wood-destructive fungi and insects 7% of water-dilutable neutralized alkyd resin
1.5–3% of 2,5-dimethylfuran-3-carboxylic acid N-methoxy-N-cyclohexylamide
0.50% of gamma-hexachlorocyclohexane
2.00% of an adduct of nonylphenol +8–11 moles of ethylene oxide
84.50–81.50% of water
3% of butylglycol
1.5–3% of a gasoline fraction (boiling range 80°–220° C.)

(2) Pigmented wood-preservative glaze, affording preventive protection against wood-destructive fungi and insects 20% of water-dilutable neutralized alkyd resin
1–2% of 2,5-dimethylfuran-3-carboxylic acid N-methoxy-N-cyclohexylamide
0.50% of gamma-hexachlorocyclohexane
1.00% of an adduct of nonylphenol +8–11 moles of ethylene oxide
2.00–5.00% of pigment or pigment formulation
1.00–2.00% of cobalt, manganese and/or lead octoate
68.50–62.50% of water
1–2% of a gasoline fraction (boiling range 80°–220° C.)
5% of butylglycol (3) Thick glaze providing preventive protection against wood-destructive fungi and insects 28% of water-dilutable neutralized alkyd resin
1–2% of 2,5-dimethylfuran-3-carboxylic acid N-methoxy-N-cyclohexylamide
0.50% of gamma-hexachlorocyclohexane
1.00% of an adduct of nonylphenol +8–11 moles of ethylene oxide
2.00–5.00% of pigment or pigment formulation
2.00% of Co, Mn and/or Pb octoate
52.50–47.50% of water
12% of butylglycol
1–2% of a gasoline fraction (boiling range 80°–220° C.

(4) 7.0% of water-dilutable neutralized alkyd resin 0.5–1.5% of tributyl-tin benzoate
0.5% of gamma-hexachlorocyclohexane
2.0% of an adduct of nonylphenol +8–11 moles of ethylene oxide
85.50–83% of water
3.0% of butylglycol
1.5–3.0% of a gasoline fraction (boiling range 80°–220° C.)

(5) 20.0% of water-dilutable neutralized alkyd resin 0.5–1.5% of tributyl-tin naphthenate
0.5% of gamma-hexachlorocyclohexane
1.0% of an adduct of nonylphenol +8–11 moles of ethylene oxide
2.0–5.0% of pigment or pigment formulation
1.0–2.0% of cobalt, manganese and/or lead octoate
69.0–63.0% of water
1.0–2.0% of a gasoline fraction (boiling range 80°–220° C.)
5.0% of butylglycol (6) 28.0% of water-dilutable neutralized alkyd resin 1.5–4.0% of pentachlorophenol laurate
0.5% of gamma-hexachlorocyclohexane
1.0% of an adduct of nonylphenol +8–11 moles of ethylene oxide
2.0–5.0% of pigment or pigment formulation
2.0% of cobalt, manganese and/or lead octoate
52.0–45.5% of water
12.0% of butylglycol
1.0–2.0% of a gasoline fraction (boiling range 80°–220° C.)

(7) 7.0% of water-dilutable neutralized alkyd resin 1.5–3.0% of the potassium salt of N-cyclohexyl-N-hydroxydiazenium oxide
0.50% of gamma-hexachlorocyclohexane
2.0% of an adduct of nonylphenol +8–11 moles of ethylene oxide
84.5–81.5% of water
3.0% of butylglycol
1.5–3.0% of a gasoline fraction (boiling range 80°–220° C.)

(8) 7.0% of water-dilutable neutralized alkyd resin 0.75–1.5% of 2,5-dimethylfuran-3-carboxylic acid N-methoxy-N-cyclohexylamide
0.5–1.0% of the Na salt of 2-mercaptobenthiazole
0.5% of gamma-hexachlorocyclohexane
2.0% of an adduct of nonylphenol +8–11 moles of ethylene oxide
84.75–82.0% of water
3.0% of butylglycol
1.5–3.0% of a gasoline fraction (boiling range 80°–220° C.)

(9) 7.0% of water-dilutable neutralized alkyd resin 0.75% of 2,5-dimethylfuran-3-carboxylic acid N-methoxy-N-cyclohexylamide
0.5–1.0% of the Na salt of 8-hydroxyquinoline
0.5% of gamma-hexachlorocyclohexane
2.0% of an adduct of nonylphenol +8–11 moles of ethylene oxide
84.75–82.0% of water
3.0% of butylglycol
1.5–3.0% of a gasoline fraction (boiling range 80°–220° C.)

(10) 7.0% of water-dilutable neutralized alkyd resin 0.75–3.0% of 2,5-dimethylfuran-3-carboxylic acid N-methoxy-N-cyclohexylamide
0.5% of 2-(methoxycarbonylamino)-benzimidazole
0.5% of gamma-hexachlorocylohexane 2.0% of an adduct of nonylphenol +8-11 moles of ethylene oxide
84.75-81.5% of water 3.0% of butylglycol
1.5-3.0% of a gasoline fraction (boiling range 80°-220° C.).

The novel wood preservatives are used in a conventional manner, for example by brushing, dipping or spraying the wood. They afford reliable protection of the treated wood against destruction of discoloration by fungi or destruction by insects. The amount of wood preservative to be employed in each individual case depends on the active ingredient concentration of the preservative and should be such that the amount of preservative with which the wood is treated contains the amount of active ingredient corresponding to the conventionally employed amount of the same ingredient.

We claim:

1. A wood preservative which consists essentially of an aqueous solution containing from 5 to 40% by weight of a neutralized alkyd resin produced from phthalic acid or phthalic anhydride, glycerol and a saturated fatty acid and from 0.5 to 5% by weight of a water insoluble fungicidal or insecticidal active ingredient selected from the group consisting of 2,5-dimethyl-furan-3-carboxylic acid N-methoxy-N-cyclohexylamide, tributyl-tin benzoate, tributyl-tin naphthenate, gamma-hexachlorocylohexane, pentachlorophenol laurate, 2-methoxycarbonylamino-benzimidazole or a mixture of these active ingredients wherein the solvent system consists essentially of water.

2. A wood preservative as claimed in claim 1, wherein the active ingredient is 2,5-dimethylfuran-3-carboxylic acid N-methoxy-N-cyclohexylamide.

3. A wood preservative as claimed in claim 1, which additionally contains an alkylphenol/alkylene oxide adduct.

4. A wood preservative as defined in claim 1 which includes up to 10% of an organic liquid.

5. A process for preserving wood from attack by fungi or insects, wherein the wood is treated with an aqueous solution containing from 5 to 40% by weight of a neutralized alkyd resin produced from phthalic acid or phthalic anhydride, glycerol and a saturated fatty acid and from 0.5 to 5% by weight of a water insoluble fungicidal or insecticidal active ingredient selected from the group consisting of 2,5-dimethylfuran-3-carboxylic acid N-methoxy-N-cyclohexylamide, tributyl-tin benzoate, tributyl-tin naphthenate, gamma-hexachlorocyclohexane, pentachlorophenol laurate, 2-methoxycarbonyl aminobenzimidazole or a mixture of these active ingredients wherein the solvent system consists essentially of water.

* * * * *